United States Patent [19]

Carpentier et al.

[11] Patent Number: 4,865,600
[45] Date of Patent: Sep. 12, 1989

[54] MITRAL VALVE HOLDER

[75] Inventors: Alain Carpentier, Paris, France; Victor E. Koik, Canoga Park; Ernest Lane, Huntington Beach, both of Calif.

[73] Assignee: Baxter International Inc., Deerfield, Ill.

[21] Appl. No.: 295,993

[22] Filed: Aug. 25, 1981

[51] Int. Cl.$^4$ .......................... A61F 2/24; A61B 17/00
[52] U.S. Cl. ........................................ 623/2; 623/900; 128/303 R
[58] Field of Search ............ 3/1.5; 128/303 R, 334 R, 128/335; 623/2, 900

[56] References Cited

U.S. PATENT DOCUMENTS

| | | | |
|---|---|---|---|
| 3,099,016 | 7/1963 | Edwards | 623/2 X |
| 3,263,239 | 8/1966 | Edwards et al. | 623/2 |
| 3,365,728 | 1/1968 | Edwards et al. | 623/2 |
| 3,466,671 | 9/1969 | Siposs | 623/2 |
| 3,509,582 | 5/1970 | Pierie | 623/2 |
| 3,534,410 | 10/1970 | Raible | 623/2 |
| 3,570,014 | 3/1971 | Hancock | 623/2 |
| 3,656,185 | 4/1972 | Carpentier | 623/2 |
| 3,710,744 | 1/1972 | Goodenough et al. | 3/1.5 X |
| 3,723,996 | 4/1973 | Raible et al. | 623/2 |
| 3,755,823 | 9/1973 | Hancock | 3/1.5 |
| 4,106,129 | 8/1978 | Carpentier et al. | 3/1.5 |

FOREIGN PATENT DOCUMENTS 2011259A 7/1979 United Kingdom .................... 623/2

OTHER PUBLICATIONS

"Star-Edwards and Carpentier-Edwards Ancillary Equipment for Cardiac Prosthesis", (4 page brochure), Oct. 1976, pp. 1-4, Edwards Laboratories.
"Instructions for Use of the Handle/Holder Assembly for the Carpentier-Edwards Aortic Bioprosthesis", Edwards Laboratories Brochure, Feb. 1980, pp. 1-2.
"A Suture Holder and Separator Attachment to the Starr-Edwards Prosthetic Valve Holders", by J. T. Grismer et al., Surgery, Gynecology and Obstetrics, Mar. 1965, pp. 583-584.
"A Method for Insertion of a Stented Xenograft Valve in the Atrioventricular Position", by George Stefanic et al., Annals of Thoracic Surgery, Jan.-Jun. 1976, pp. 166-167.
"Stented Xenograft Valve Insertion", by Edward Proctor et al., The Annals of Thoracic Surgery, vol. 29, No. 4, Apr. 1980, pp. 385-386.
"Entanglement of Sutures with Struts of Mitral Bioprosthesis: How To Prevent it", by N. Spampinato et al., Annals of Thoracic Surgery, Jan.-Jun. 1981, pp. 478-479.
"Prevention of Strut-Snagging during Mitral Valve Replacement with Stented Tissue Valves", by J. B. Borman et al., Annals of Thoracic Surgery, Jul.-Dec. 1981, pp. 209-210.
"Safer Insertion of Ionescu-Shiley Valves in the Atrioventricular Position", by G. Morritt et al., Annals of Thoracic Surgery, Jan.-Jun. 1982, pp. 94-95.

Primary Examiner—Ronald L. Frinks
Attorney, Agent, or Firm—Willian Brinks Olds Hofer Gilson & Lione

[57] ABSTRACT

An assembly comprising a prosthetic heart valve having a plurality of commissure supports which are deflectable radially inwardly and a valve holder which includes inner and outer holder members mounted for movement toward and away from each other. The valve holder is attached to the heart valve by sutures which extend from the outer holder member to the commissure supports and then between the commissure supports. When a handle is attached to the other holder member, the holder members are forced apart to tension the sutures to deflect the commissure supports radially inwardly. Portions of the sutures extend between the commissure supports to form a suture loop guard.

16 Claims, 4 Drawing Sheets

MITRAL VALVE HOLDER

BACKGROUND OF THE INVENTION

Prosthetic heart valves are either mechanical or of the type which include commissure supports and valve leaflets. Mechanical heart valves typically include a ball valve. The other type of heart valve typically includes a frame, valve leaflets mounted on the frame and a suture ring. The valve leaflets may be formed of either biological or synthetic material. This form of heart valve has commissure supports which project away from the suture ring and terminate in free end portions. Thus, each of the commissure supports forms a projection or strut. This invention relates to an assembly which includes a prosthetic heart valve of the type which has commissure supports and valve leaflets.

Prosthetic heart valves are commonly used to replace diseased valves within the human heart. In replacing a mitral valve, it is common practice for the physician to manually position the mitral valve and sew the suture ring to heart tissue using sutures and an appropriate suturing technique. Manual handling of the valve during valve replacement increases the danger of damaging the valve. In addition, the replacement valve must be properly oriented in the heart, and manual orientation and placement are difficult.

More importantly, however, damage to the left ventricle can result from mitral valve replacement, and this problem is discussed in Katske, Gordon M.D. et al, "Posterior Midventricular Rupture After Mitral Valve Replacement", *The Annals Of Thoracic Surgery*, Volume 27, No. 2, February 1979, and Nunez, L. M.D. et al, "Delayed Rupture Of The Left Ventricle After Mitral Valve Replacement With Bioprosthesis", *The Annals Of Thoracic Surgery*, Volume 27, No. 5, May, 1979. The consequences of ventricular rupture can, of course, be fatal. As reported by these authors, the damage to the left ventricle is believed to be the result of impalement of a strut or commissure support against the left ventricle.

Another serious problem with mitral valve replacement is suture looping, and this problem is referred to in the Katske et al publication referred to above. Suture looping means that the suture which is used to attach or mount the valve to the heart tissue is inadvertently wrapped around one or more of the commissure supports or struts. If this occurs, the looped suture interferes with valve operation.

SUMMARY OF THE INVENTION

This invention provides a valve holder for a prosthetic heart valve of the type which includes commissure supports and valve leaflets of biological or synthetic materials. The valve holder is particularly adapted for use with a prosthetic mitral valve Mitral valves of this type are used for replacement of diseased mitral and tricuspid valves The valve holder-heart valve assembly of this invention has a feature which permits the commissure supports to be deflected radially inwardly so as to materially reduce the likelihood of harmful contact with the left ventricle during mitral valve replacement. The assembly of this invention also includes a suture loop guard which reduces the likelihood of suture looping and consequent malfunctioning of the replacement valve.

Valve holders for mechanical heart valves and for bioprosthetic aortic heart valves are known However, these prior art valve holders are not suited for use with a bioprosthetic mitral valve. Moreover, these prior art valve holders have no means to prevent suture looping or to deflect the commissure supports so as to avoid damage to the left ventricle.

This invention provides an assembly which includes a prosthetic heart valve, a valve holder attached to the heart valve, and means for deflecting at least one of the commissure supports of the heart valve radially inwardly. Thus, during the replacement procedure, one or more of the commissure supports are deflected radially inwardly to a position where they are much less likely to cause damage to the left ventricle. The commissure supports are resilient, and so, when the valve holder is removed after valve replacement, the commissure supports return to their normal position.

Various techniques can be used to deflect the commissure supports. However, the commissure support deflection technique can advantageously be combined with the suture loop guard. One way to accomplish this is to utilize elongated flexible means, such as sutures, extending between the commissure supports to provide a suture loop guard. Preferably, the sutures extend between the free end portions of the commissure supports where they will be most effective in preventing suture looping. With this construction, commissure support deflection can be obtained by tensioning the suture loop guard to draw one or more of the commissure supports radially inwardly. Preferably, all of the commissure supports are deflected radially inwardly.

Although the holder may take different forms, in a preferred construction, it includes inner and outer holder members, with the inner member being between the outer holder member and the heart valve. The holder members are mounted for movement toward and away from each other, and movement of the holder members away from each other can advantageously be used to provide the motion necessary for commissure support deflection. This can be accomplished, for example, by coupling the elongated flexible means to the outer holder member so that movement of the outer holder member away from the inner holder member tensions the elongated flexible means to deflect the commissure supports.

Although movement of the holder members away from each other can be brought about in various different ways, in a preferred construction this is accomplished by attaching the handle to the valve holder. Thus, the deflection of the commissure supports is made responsive to the attachment of the handle to the holder. In other words, the means for deflecting the commissure supports radially inwardly is actuated or operated by the handle.

More specifically, this can be advantageously accomplished by providing a threaded end portion on the handle and a cooperating threaded portion on the outer holder member, with the inner holder member being exposed through the threaded portion of the outer holder member. Accordingly, attaching the handle to the outer holder member enables the handle to engage the inner holder member to move the holder members away from each other. The amount which the holder members are separated is, therefore, a function of the extent to which the threaded end portion of the handle is threaded into the threaded portion of the outer holder member. Suitable locking means, such as a jam nut, can be used to fix the two threaded portions in any desired angular position. This enables the handle to be oriented with respect to the heart valve and permits the amount of commissure support deflection to be controlled.

In use, the heart valve is controlled and positioned utilizing the handle while the suture ring of the heart valve is sewn in place. Next, the sutures attaching the holder to the valve are cut to enable removal of the holder and the handle as a unit leaving the heart valve in position in the heart.

The invention, together with additional features and advantages thereof, may best be understood by reference to the following description taken in connection with the accompanying illustrative drawing.

DESCRIPTION OF THE PREFERRED EMBODIMENT

Figure 1:
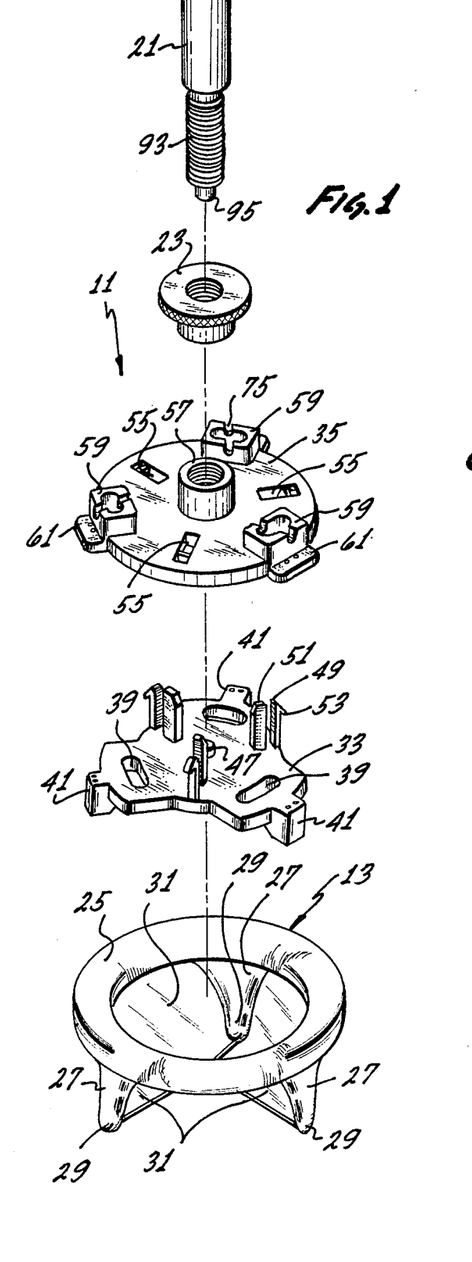
FIG. 1 is an exploded perspective view of an assembly, with the sutures removed, constructed in accordance with the teachings of this invention.
Figure 2:
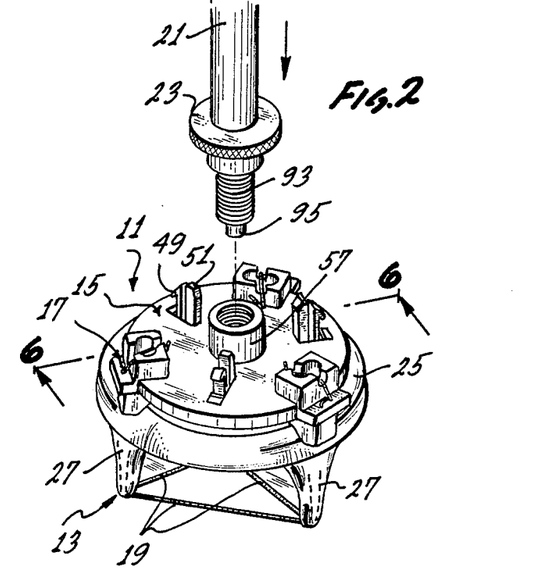
FIG. 2 is a perspective view of the assembly with the handle about to be attached to the outer holder member.
Figure 3:
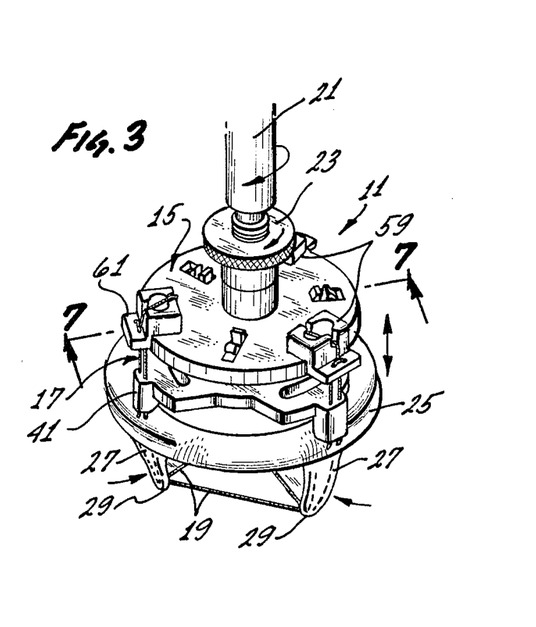
FIG. 3 is a perspective view similar to FIG. 2, with the handle attached to the outer holder member.

FIGS. 1-3 show one form of an assembly 11 constructed in accordance with the teachings of this invention. Generally, the assembly 11 comprises a prosthetic heart valve 13, a valve holder 15, elongated flexible means 17 for attaching the heart valve to the holder and defining a suture loop guard 19, a handle 21 and locking means in the form of a jam nut 23.

The heart valve 13 is a mitral heart valve and may be of conventional construction Thus, the heart valve 13 is of the type which includes an essentially flat, annular suture ring 25, three struts or commissure supports 27 projecting generally axially from the suture ring 25 and terminating in free end portions 29 and three valve leaflets 31 which may be formed of synthetic material or tissue. Heart valves, such as the valve 13, typically include a frame of wire or other suitable material, and the commissure supports 27 are resilient so that they can be deflected radially inwardly.

Figures 4, 5, 6, 7:
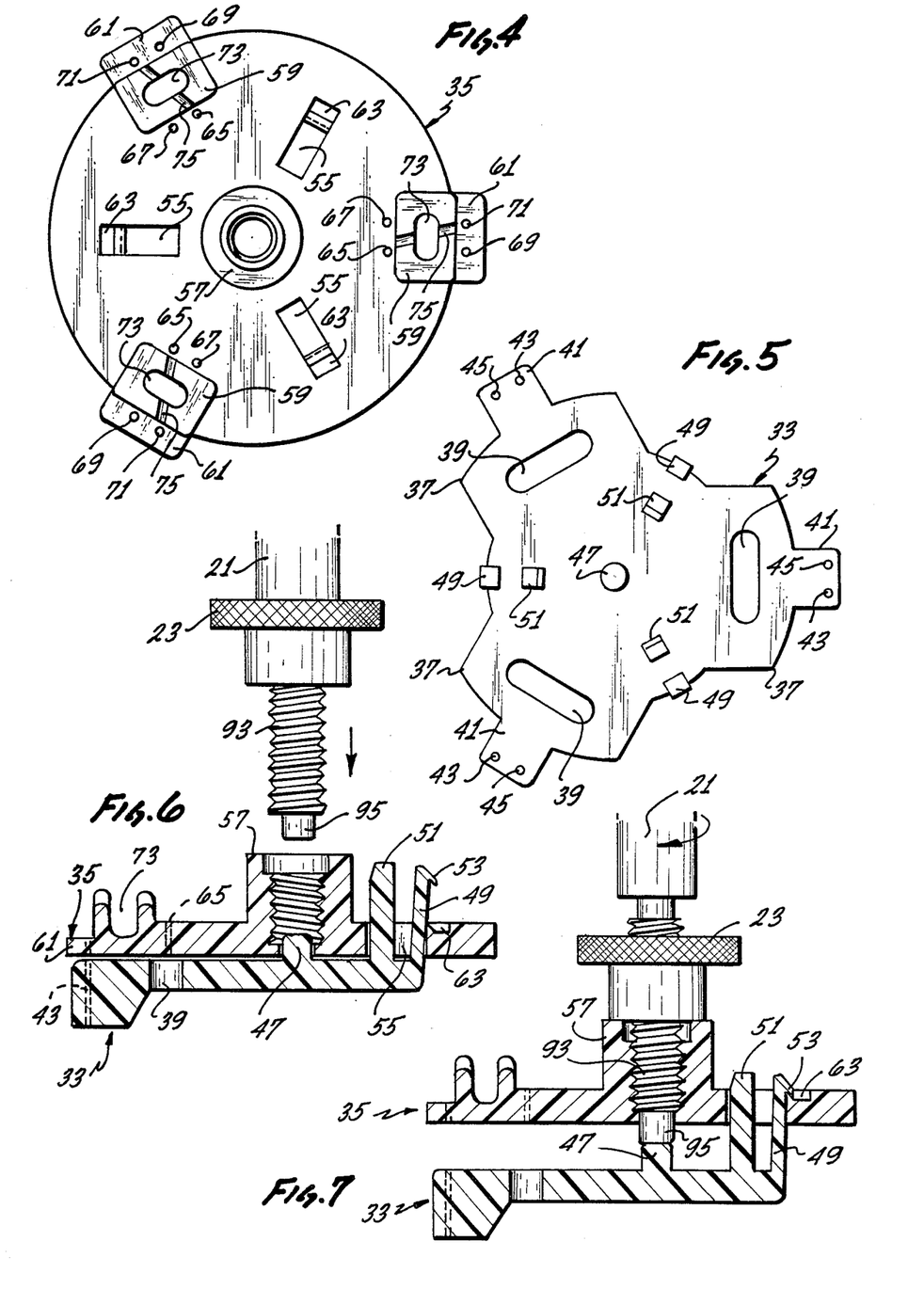
FIGS. 4 and 5 are top plan views of the outer and inner holder members, respectively.
FIGS. 6 and 7 are enlarged sectional views taken generally along lines 6—6 and 7—7, respectively, of FIGS. 2 and 3 and illustrating how the handle can be used to move the holder members apart.

In the specific embodiment illustrated, the valve holder 15 comprises an inner holder member or plate 33 and an outer holder member or plate 35, each of which is constructed of a relatively rigid, biocompatible material For example, each of the plates 33 and 35 may be integral and injection molded from a suitable plastic material. As best shown in FIGS. 1 and 5, the inner plate 33 may include three radial projections 37 which are equally spaced circumferentially and which include slots 39. Each of the projections 37 terminate radially outwardly in a lug 41 having apertures 43 and 45. The inner plate 33 has an axial upstanding abutment 47 and three sets of axially extending mounting rails 49 and 51, with the mounting rails 49 being resiliently deflectable radially and having an overhanging lip 53 (FIGS. 6 and 7).

In the embodiment illustrated, the outer plate is in the form of a circular disc having three slots 55 (FIGS. 1 and 4), an axially protruding internally threaded boss 57, three axially protruding blocks 59 and three radial flanges 61. The outer plate has recesses 63 which lie contiguous and radially outwardly from each of the slots 55.

Suture apertures 65 and 67 are provided slightly radially inwardly from each of the blocks 59, and suture apertures 69 and 71 are provided in each of the flanges 61. Each of the blocks 59 has an axially opening pocket 73, and a groove 75 in each of the blocks 59 extends along a line from the associated aperture 65 to the associated aperture 71.

To assemble the valve holder 15, the mounting rails 49 and 51 are inserted through the slots 55 of the outer plate 35 as shown in FIGS. 2, 3 and 6. The mounting rails 49 can be deflected radially inwardly to permit the rails 49 and 51 to be snap fit into the slots 55, and the lips 53 on the rails 49 prevent separation of the plates 33 and 35. Thus, the plates 33 and 35 are mounted for limited axial movement relative to each other. In addition, in the assembled condition, the blocks 59 are axially aligned with the lugs 41, respectively, and each set of the apertures 69 and 71 are axially aligned with the associated set of apertures 43 and 45, respectively. The abutment 47 projects into the boss 57 as shown in FIG. 6.

Figures 8, 8A, 9:
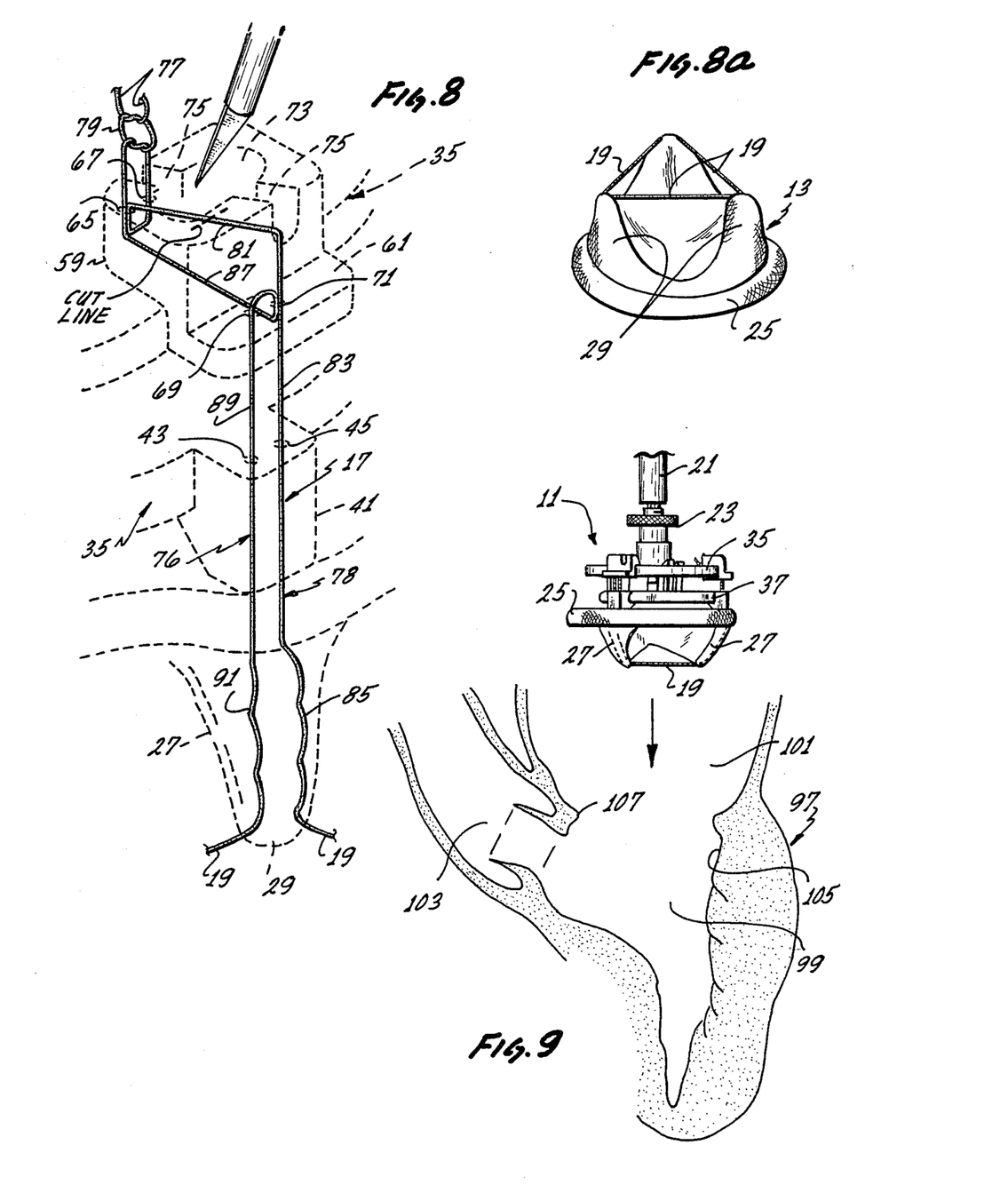
FIG. 8 is an enlarged fragmentary perspective view illustrating one manner in which the sutures forming the elongated flexible means can be utilized. The other portions of the assembly are shown in dashed lines.
FIG. 8a is a perspective view of the heart valve and the suture loop guard.
FIG. 9 shows how the holder and handle can be used to position the heart valve for insertion in the mitral position in a human heart.

The elongated flexible means 17 can be used, as shown by way of example, in FIGS. 2, 3 and 8 to attach the valve holder 15 to the heart valve 13. Although different constructions can be used, in the form illustrated in FIG. 8, the elongated flexible means 17 comprises three sutures, with only two of such sutures 76 and 78 being shown in FIG. 8. The sutures 76 and 78 have opposite ends 77 which are tied off to form a knot 79 immediately above and between two of the apertures 65 and 67. From the knot 79, the suture 78 extends down through the aperture 67, along the lower face of the outer plate 35 and back up through the aperture 65. A length 81 of the suture 78 extends from the upper opening of the aperture 65 across both sections of the groove 75 and across the pocket 73 to a length 83 which extends generally axially through substantially the full length of one of the commissure supports 27 to the free end portion 29 of the commissure support. The commissure support 27 shown in FIG. 8 is axially aligned with the block 59 and the lug 41. The suture 78 then extends from the commissure support 27 shown in FIG. 8 to the adjacent commissure support 27, and the portion of the suture 78 between these commissure supports forms a portion of the suture loop guard 19.

The suture 76 on the opposite side of the knot 79 extends down through the aperture 65 and has a length 87 that extends along the bottom face of the outer plate 35 to the bottom opening of the aperture 71. The suture 76 then extends up through the aperture 71, across a short radial span of the upper face of the flange 61 and down through the aperture 69. A length 89 of the suture 76 extends from the aperture 69 axially through the aperture 43, which is aligned axially with the aperture 69, to a length 91 which extends axially through the commissure support 27 to the free end portion 29. The suture 76 then passes out through the free end portion 29 and extends to the adjacent commissure support in the other direction, with such portion of the suture 76 forming a portion of the suture loop guard 19.

The manner in which the elongated flexible means 17 cooperates with the holder 15 at the other blocks 59 and lugs 41 is identical to the arrangement shown in FIG. 8. Thus, the elongated flexible means 17 extends between the free end portions 29 of adjacent commissure supports 27 to form a rail or guard between each adjacent commissure support (FIG. 8a).

The valve holder 15 is disposable, but the handle 21 is preferably reusable and may be constructed of a suitable metal, such as stainless steel. In the embodiment illustrated, the handle 21 has a threaded end portion 93 on which the jam nut 23 can be threaded and which can be threaded into the internally threaded boss 57 on the outer plate 35. The end of the handle 21 defines an abutment 95 which is engageable with the abutment 47 on the inner plate 33 when the threaded end portion 93 is threaded a predetermined distance into the boss 57. Accordingly, by threading the handle 21 into the boss 57, the engagement between the abutments 47 and 95 drives the plates 33 and 35 apart as shown in FIG. 7. In FIG. 7, the plates 33 and 35 have been moved apart the maximum amount, and the lips 53 on the mounting rails 49 engage the edges of the recesses 63 to prevent further separation of the plates. Of course, the plates 33 and 35 can be moved apart less than the full distance permitted by the lips 53. The jam nut 23 can be tightened down on the boss 57 to lock the handle 21 in the desired position.

In use of the assembly 11, the handle 21 may be bent by the physician to facilitate its use during holding and placement of the heart valve 13. The handle 21 is then attached to the valve holder 15 as described above, and the handle can be angularly oriented with respect to the valve 13 as may be desired by the physician. The jam nut 23 is screwed down against the boss 57 to lock the handle in the desired orientation with respect to the valve 13.

Movement of the outer plate 35 away from the inner plate 33 raises the lengths 83 and 89 of the sutures at each of the commissure supports 27 to tension the sutures and the suture loop guard 19. Because the sutures 76 and 78 are essentially not extendible axially, the tensioning of the suture loop guard 19 forces the commissure supports 27 radially inwardly against their inherent resilience as shown in FIG. 3.

FIG. 9 shows the assembly 11 being advanced into position for insertion into a human heart 97. The portion of the heart 97 illustrated includes the left ventricle 99, the left atrium 101 and the aorta 103. The left ventricle has a ventricle wall 105 (FIGS. 9–11) and the heart has an annulus 107 to which the suture ring 25 is to be sewn.

Figures 10, 11:
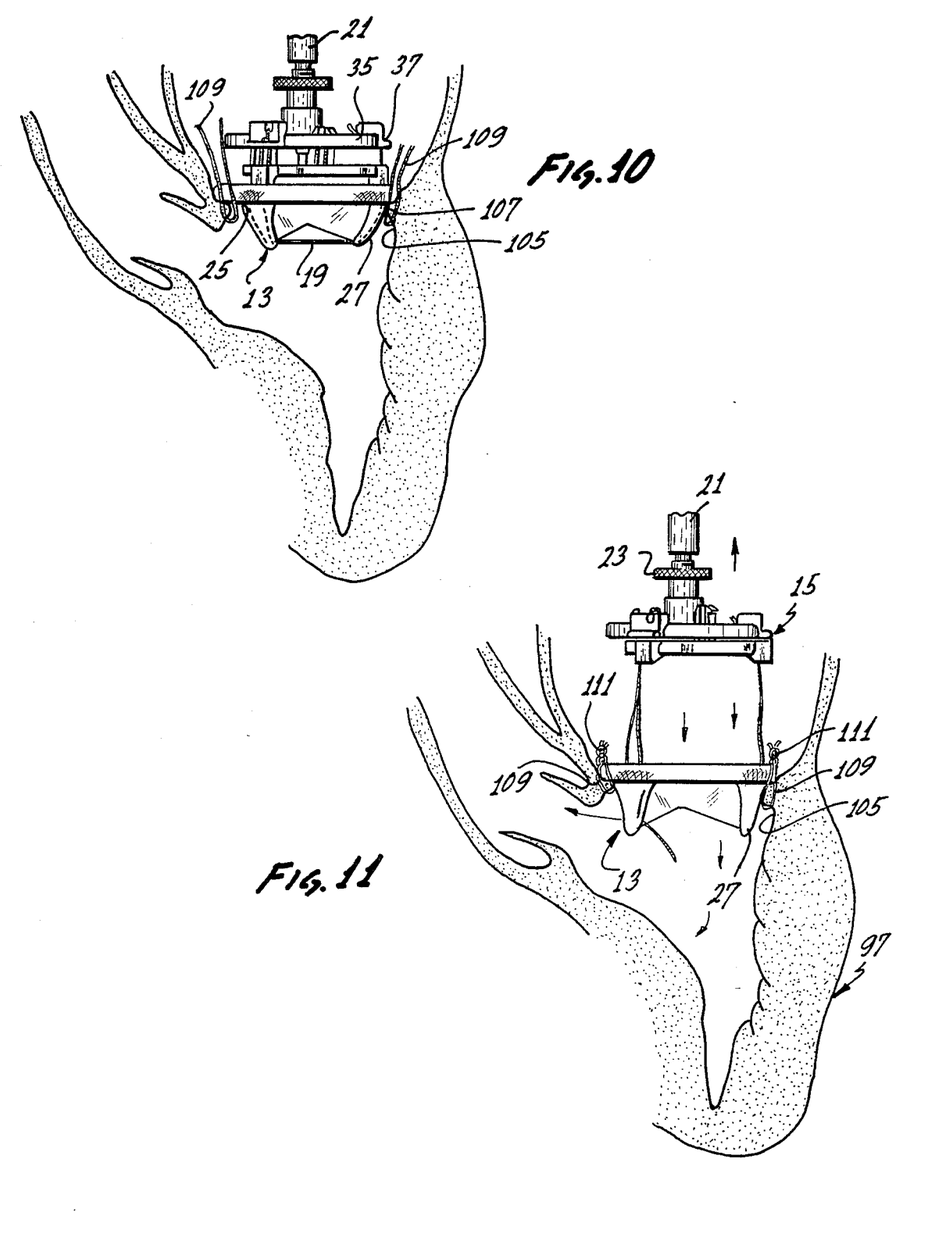
FIG. 10 and FIG. 11 are side elevational views showing the suturing of the heart valve in place and the removal of the handle and holder from the heart valve, respectively.

Proper alignment of the heart valve 13 to avoid interfering with flow to the aorta requires angularly orienting the valve so that one of the commissure supports 27 is near the ventricle wall 105 as shown in FIGS. 10 and 11. Because space at this location is at a minimum, there is danger of damaging the ventricle wall 105 during insertion of the valve 13. However, by deflecting the commissure supports 27 radially inwardly, insertion of the valve 13 through the annulus 107 is facilitated, and the likelihood of harmful contact between the ventricle wall 105 and the adjacent commissure support 27 is minimized.

With the valve 13 properly positioned, the surgeon sews the suture ring 25 to the annulus 107 using sutures 109 and known suturing techniques. During this suturing operation, the suture loop guard 19 materially reduces the likelihood of looping of one of the sutures 109 around the commissure supports 27 so as to impair operation of the heart valve 13.

When suturing has been completed, the sutures 109 are tied off in knots 111 (FIG. 11), and the length 81 (FIG. 8) of each of the sutures is cut in each of the pockets 73. This permits the handle 21, and the valve holder 15 to be withdrawn as shown in FIG. 11 leaving the valve 13 in position in the heart. Because of the knots 77, the elongated flexible means is also withdrawn in its entirety along with the valve holder 15 so that only the heart valve 13 and the sutures 109 remain in the heart. Of course, cutting of the suture 17 releases the tension on the suture loop guard 19 so that the commissure supports 27 resiliently return to their normal position Thereafter, the holder 15 is removed from the handle 21 and disposed of. The handle 21 may be retained for future use.

Although an exemplary embodiment of the invention has been shown and described, many changes, modifications and substitutions may be made by one having ordinary skill in the art without necessarily departing from the spirit and scope of this invention.

We claim:

1. An assembly comprising:
   a prosthetic heart valve having a plurality of commissure supports and valve leaflets, said commissure supports terminating in free ends and at least one of said commissure supports being deflectable radially inwardly;
   a valve holder;
   means for attaching the heart valve to the valve holder with the valve holder being remote from the free ends of the commissure supports; and
   means at least partially on the valve holder for deflecting at least said one commissure support radially inwardly;
   said holder including inner and outer holder members with the inner holder member being between the outer holder member and the heart valve, means for mounting the holder members for movement toward and away from each other, said deflecting means including elongated flexible means coupled to the outer holder member and at least said one commissure support whereby movement of the outer holder member away from the inner holder member tensions the elongated flexible means to deflect said one commissure support radially inwardly.

2. An assembly comprising:
   a prosthetic heart valve having a plurality of commissure supports and valve leaflets, said commissure supports being deflectable radially inwardly;
   a valve holder including inner and outer holder members with the inner holder member being between the outer holder member and the heart valve and means for mounting the holder members for movement toward and away from each other; and
   elongated flexible means coupled to the outer holder member and at least two of said commissure supports so that movement of the outer holder member away from the inner holder member tensions the elongated flexible means to deflect at least said two commissure supports radially inwardly.

3. An assembly as defined in claim 2 including means for moving said outer holder member away from said inner holder member.

4. An assembly as defined in claim 3 wherein said moving means includes an elongated handle having a threaded end portion and a cooperating threaded portion on said outer holder member, said inner holder member being exposed through said threaded portion of said outer holder member whereby threadedly attaching the handle to the outer holder member enables the handle to engage the inner holder member to move the holder members away from each other.

5. An assembly as defined in claim 4 including means for locking said threaded portions together at any desired relative angular orientation of said threaded portions whereby said holder members can be moved away from each other a desired amount and locked in position.

6. An assembly as defined in claim 2 wherein said commissure supports terminate in free end portions and a portion of said elongated flexible means extends between said free end portions to form a suture loop guard.

7. An assembly comprising:
a prosthetic heart valve having a suture ring, a plurality of commissure supports projecting from the suture ring and terminating in free end portions and a plurality of valve leaflets;
a valve holder;
elongated flexible means for attaching the valve holder to the heart valve with said suture ring being between the valve holder and the commissure supports; and
a portion of said elongated flexible means extending between said free end portions of said commissure supports to form a suture loop guard;
said elongated flexible means including a section which extends from the valve holder generally axially through a first of the commissure supports and exits at the free-end portion thereof.

8. An assembly comprising:
a prosthetic heart valve having a plurality of commissure supports and valve leaflets, at least one of said commissure supports being deflectable radially inwardly and each of said commissure supports having a free end;
a valve holder including first and second holder members and means for mounting the first holder member for movement relative to the second holder member;
means for attaching the heart valve to the valve holder with the valve holder being remote from the free ends of the commissure supports; and
means responsive to the movement of the first holder member relative to the second holder member for deflecting at least one of the commissure supports radially inwardly.

9. An assembly as defined in claim 8 including a rotatable handle attachable to the valve holder and means responsive to the rotation of the handle for moving the first holder member relative to the second holder member to deflect at least said one commissure support radially inwardly.

10. An assembly as defined in claim 9 including means for retaining said handle at any one of a plurality of angular orientations whereby said valve holder members can be retained in position.

11. An assembly as defined in claim 8 wherein said deflecting means includes elongated, flexible means extending between at least two of said commissure supports and drivingly coupled to said first holder member, said two commissure supports being deflectable whereby movement of the first holder member relative to the second holder member tensions the elongated flexible means to deflect at least said two commissure supports radially inwardly.

12. An assembly as defined in claim 11 including a handle attachable to the valve holder for moving the first holder member relative to the second holder member.

13. An assembly as defined in claim 11 wherein said second holder member includes three radially extending projections and there are three of said commissure supports, said projections and said commissure supports being generally in axial alignment, said assembly including a handle attachable to the first valve holder and being rotatable to move the first valve holder relative to the second valve holder, said attaching means including at least a portion of said elongated flexible means.

14. An assembly as defined in claim 8 including a handle attachable to the valve holder for moving the first holder member relative to the second holder member.

15. An assembly comprising:
a prosthetic heart valve having a plurality of commissure supports and valve leaflets, at least one of said commissure supports being deflectable radially inwardly;
a valve holder;
means for attaching the heart valve to the valve holder;
means for deflecting at least said one commissure support radially inwardly;
a handle;
means for attaching the handle to the valve holder; and
said deflecting means being responsive to the attachment of the handle to the holder to deflect said one commissure support radially inwardly.

16. An assembly comprising:
a prosthetic heart valve having a plurality of commissure supports and valve leaflets, at least one of said commissure supports being deflectable radially inwardly;
a valve holder;
means for attaching the heart valve to the valve holder;
a rotatable handle attachable to the valve holder; and
means responsive to the rotation of the handle for deflecting at least said one commissure support radially inwardly.

* * * * *

UNITED STATES PATENT AND TRADEMARK OFFICE
CERTIFICATE OF CORRECTION

PATENT NO. : 4,865,600

DATED : September 12, 1989

INVENTOR(S) : Alain Carpentier et al.

It is certified that error appears in the above-identified patent and that said Letters Patent is hereby corrected as shown below:

On the title page in column 2, line 9, of the Abstract, please delete "other" and substitute therefor --outer--.

In column 1, line 57, after "valve" please insert --.--.

In column 1, line 59, after "valves" please insert --.--.

In column 2, line 2, after "known" please insert --.--.

In column 3, line 54, after "construction" please insert --.--.

UNITED STATES PATENT AND TRADEMARK OFFICE
CERTIFICATE OF CORRECTION

PATENT NO. : 4,865,600

DATED : September 12, 1989

INVENTOR(S) : Alain Carpentier et al.

It is certified that error appears in the above-identified patent and that said Letters Patent is hereby corrected as shown below:

In column 3, lines 67 and 68, after "material" please insert --.--.

Signed and Sealed this

Fourteenth Day of July, 1992

Attest:

DOUGLAS B. COMER

Attesting Officer

Acting Commissioner of Patents and Trademarks